United States Patent [19]

Hess et al.

[11] 4,353,887

[45] Oct. 12, 1982

[54] DIVISIBLE TABLET HAVING CONTROLLED AND DELAYED RELEASE OF THE ACTIVE SUBSTANCE

[75] Inventors: Hans Hess, Binningen; Carlo Voellmy, Rheinfelden, both of Switzerland

[73] Assignee: Ciba-Geigy Corporation, Ardsley, N.Y.

[21] Appl. No.: 177,028

[22] Filed: Aug. 11, 1980

[30] Foreign Application Priority Data

Aug. 16, 1979 [CH] Switzerland ..................... 7514/79
May 21, 1980 [CH] Switzerland ..................... 3959/80

[51] Int. Cl.³ .................. A61K 9/20; A61K 9/22; A61K 9/24; A61K 9/28
[52] U.S. Cl. ........................ 424/15; 124/14; 124/16; 124/19; 124/21
[58] Field of Search .................. 424/15, 19–22; 426/76, 144; D28/2; D1/12

[56] References Cited

U.S. PATENT DOCUMENTS

| D.89,941 | 5/1933 | Low | D1/12 |
|---|---|---|---|
| D.91,644 | 3/1934 | Blackstone | D28/2 |
| D.98,858 | 3/1936 | Gager | D1/12 |
| D.201,497 | 6/1965 | Ninger | D16/3 |
| D.202,467 | 10/1965 | Guilmot | D28/2 |
| D.216,307 | 12/1969 | Ninger | D28/2 |
| D.224,591 | 8/1972 | Roberts | D28/2 |
| D.228,456 | 9/1973 | Ninger | D1/12 |
| D.229,049 | 11/1973 | Roberts | D16/3 |
| 1,836,604 | 12/1931 | Meyer | 426/76 |
| 2,052,376 | 8/1936 | Zellers | 424/15 |
| 2,132,690 | 10/1938 | Hilliard | 426/144 |
| 2,410,110 | 10/1946 | Taylor | 424/34 |
| 2,410,417 | 11/1946 | Anderson | 424/34 |
| 2,811,483 | 10/1957 | Aterno et al. | 424/34 |
| 2,853,420 | 9/1958 | Lowey | 424/20 |
| 2,953,497 | 9/1960 | Press | 424/20 |
| 2,996,431 | 8/1961 | Barry | 424/20 |
| 3,115,441 | 12/1963 | Hermelin | 424/34 |
| 3,166,476 | 1/1965 | Lowey | 424/20 |
| 3,336,200 | 8/1967 | Krause et al. | 424/19 |
| 4,215,104 | 7/1980 | Ullman et al. | 424/15 |

FOREIGN PATENT DOCUMENTS

| 107822 | 7/1939 | Australia | 426/144 |
|---|---|---|---|
| 249875 | 10/1966 | Austria | 424/15 |
| 352208 | 9/1937 | Italy . | |
| 8869 | of 1888 | United Kingdom | 424/15 |
| 189400 | 11/1922 | United Kingdom | 426/144 |
| 238264 | 8/1925 | United Kingdom | 426/144 |
| 993291 | 5/1965 | United Kingdom | 424/15 |
| 1246508 | 9/1971 | United Kingdom | 424/15 |
| 1368574 | 10/1974 | United Kingdom | 424/15 |

*Primary Examiner*—Shep K. Rose
*Attorney, Agent, or Firm*—Michael W. Glynn; Prabodh I. Almaula

[57] ABSTRACT

Divisible tablet having controlled and delayed release of the active substance and consisting of a compact that is optionally provided with a coating and is formed by at least one active substance in an adjunct composition that effects a delayed and controlled release of the active substance and optionally one or more additional adjunct compositions that optionally contain active substances and are arranged in longitudinal layers, the compact being of an oblong shape in which the ratio of length to width to depth is approximately 2.5 to 5: approximately 0.9 to 2:1 and the width constitutes at most ⅔ of the length, and in which one or more relatively deep dividing grooves are present which run perpendicularly to the length and the depth and have a total depth constituting from approximately ⅛ to approximately ½ of the depth of the tablet, but are at least so deep that one fracture surface area multiplied by the number of possible fragments constitutes a maximum of 15% of the surface area of the undivided tablet, the base and top faces independently of one another are planar or are convexly curved about the longitudinal axis or about parallels to this axis, the side faces are planar, the end faces can be of any shape and edges are optionally bevelled or rounded.

7 Claims, 11 Drawing Figures

Fig. 1
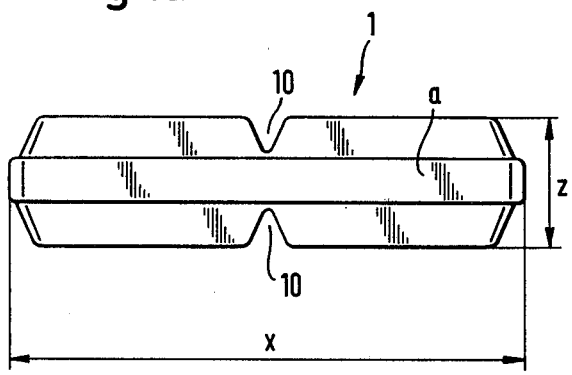
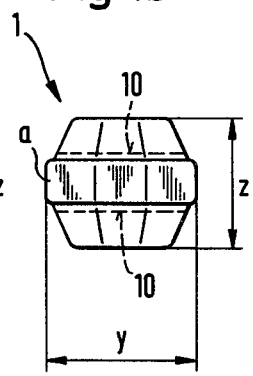
Fig. 1a
Fig. 1b
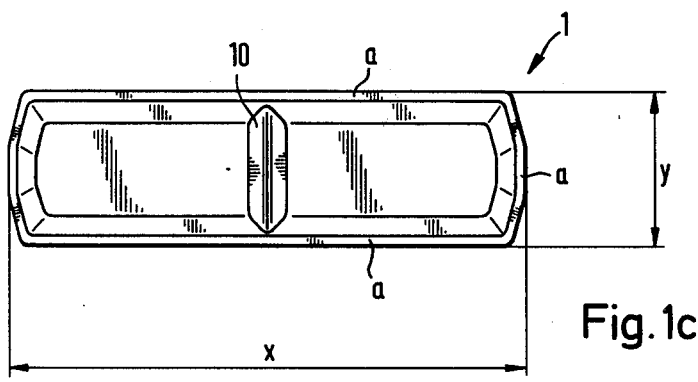
Fig. 1c

Fig. 2
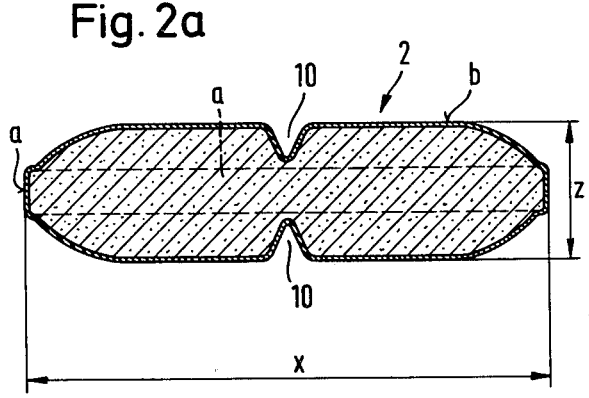
Fig. 2a
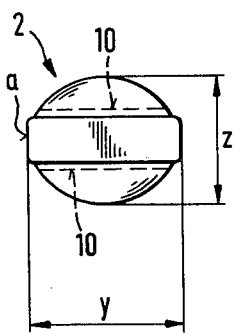
Fig. 2b
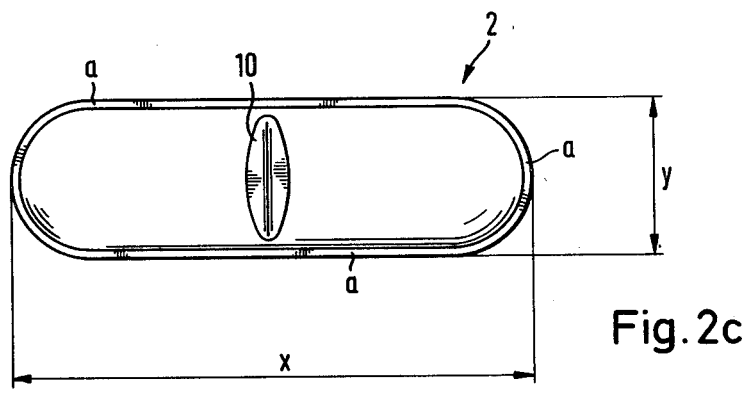
Fig. 2c

Fig. 3, c, d, e

DIVISIBLE TABLET HAVING CONTROLLED AND DELAYED RELEASE OF THE ACTIVE SUBSTANCE

The subject of the present invention is a divisible tablet having controlled and delayed release of the active substance.

Pharmaceutical forms of administration that can be administered perorally and have a delayed and controlled release of the active substance in order to maintain in the body, especially in the blood circulation, a concentration of active substance that is as long-lasting and as constant as possible, that is to say, so-called retard forms, have been known for a long time. These are especially tablets and capsules that are provided with a coating that delays and controls the release of the active substance, or in which at least a portion of the carrier and/or adjunct, in which the active substance or substances is or are distributed, allows the active substance to be released in a delayed and controlled manner.

Also customary are tablets having dividing grooves which allow medicaments to be divided more or less easily into partial doses which contain practically equal proportions of the active substance. Through the provision of relatively deep dividing grooves it is possible to render the corresponding tablets easier to break and to keep the dosage in the fragments as exact as possible. In this connection see, for example the following patent specifications: U.S. Pat. No. 3,883,647, U.S. (Design) 201,497, U.S. (Design) 202,467 and DE-AS No. 1 200 790. Furthermore, retard tablets of practically oval shape having dividing grooves of moderate depth are also commercially available.

However, in the case of tablets having delayed and controlled release of the active substance, the division of the tablet into fragments has a disadvantageous effect because when, for example, the afore-mentioned divisible retard tablet is divided, the surface area of the tablet, and thus also the partial doses, is considerably increased, for example by more than 20% in the case of one fracture surface. Consequently, the active substance release characteristics of the fragment in relation to those of the whole tablet are critically influenced. With a total surface area that has significantly been increased by the division of the tablet, the delayed and controlled release of the active substance determined experimentally for the whole tablet is altered in such a manner that the fragments either no longer exhibit these properties or exhibit them only to a partial extent. Furthermore, in the case of fragments of tablets having a coating that controls the release of the active substance, a relatively large portion of this coating is lost, so that a portion of the active substance is released more or less in an uncontrolled manner.

Accordingly, the problem being posed was that of providing a divisible retard tablet form that is readily divided into fragments which, between them, have an approximately equal content of active substance and active substance release characteristics approximating those obtained for the whole tablet; that is to say, it was necessary to find a tablet form which, on being divided, would produce the smallest possible increase, resulting from the formation of fracture surfaces, in the total surface area. In addition, care had to be taken that a tablet form of this type would still be easy to manufacture, process and pack, and also to break, while avoiding waste as far as possible. Here, it also has to be taken into account that, for example when packing by machine, especially into the preferred blister packs, tablets having a smooth surface, which can be obtained, for example, by the application of coatings (with or without the properties of controlling active substance release), are considerably easier to handle, because of their increased sliding properties, than tablets having a rough surface, for example without such coatings; that is to say, the divisible retard tablets should, if required, be able to withstand a coating process for the application of such a coating as far as possible without the formation of waste.

It has now been discovered that a divisible tablet, defined in the following, having controlled and delayed release of the active substance produces fragments in which the active substance release characteristics differ, at most, insignificantly from those of the whole tablet and which also largely fulfils the above-mentioned additional requirements. The tablet according to the invention is characterised in that it consists of a compact that is optionally provided with a coating and is formed by at least one active substance in an adjunct composition that effects a delayed and controlled release of the active substance and optionally one or more additional adjunct compositions that optionally contain active substances and are arranged in longitudinal layers, the compact being of an oblong shape in which the ratio of length to width to depth is approximately 2.5 to 5:approximately 0.9 to 2:1 and the width constitutes at most $\frac{2}{3}$ of the length, and in which one or more relatively deep dividing grooves are present which run perpendicularly to the length and depth and have a total depth of from approximately $\frac{1}{3}$ to approximately $\frac{1}{2}$ of the depth of the tablet, but are at least so deep that one fracture surface area multiplied by the number of possible fragments constitutes a maximum of 15% of the surface area of the undivided tablet; the base and top faces independently of one another are planar or are convexly curved about the longitudinal axis or about parallels to this axis, the side faces are planar, the end faces can be of any shape and edges are optionally bevelled or rounded.

The dosage unit forms according to the invention fulfil the requirements made both of divisible tablets and of retard tablets in that they are easy to break into fragments that have a practically equal, or a predetermined different, content of active substance, without the total surface area being increased in comparison with the surface area of the undivided tablet by more than 15% in the case of two possible fragments, or by more than approximately 20% in the case of three possible fragments. Surprisingly, it has been established that the impairment of the retard action for the fragments is smaller than might have been anticipated on the basis of the total surface area increased by the irregularly structured and porous fracture surfaces. These facts have the result that, from the point of view of dose and active substance release, therapy can be carried out just as accurately when using partial tablets as when using whole tablets.

In addition, it has been found that, in spite of their oblong shape and relatively deep dividing grooves, which would be expected to render processing and handling more difficult, the divisible retard tablets of the present invention have a surprisingly high strength. This renders it possible, for example, to provide divisible retard tablets according to the invention with a coating, while to a large extent avoiding waste, which coating, in addition to rendering the tablet easier to process, also lends it an additional strength which is advantageous especially when packing and, for example, when pressing the tablet out of a blister pack.

Furthermore, the surprisingly high strength, which can optionally be increased by the application of a coating, and the oblong shape have additional advantages for the divisible retard tablets according to the invention. They can readily be marked by means of embossing or printing and this can be carried out on both sides, for example with the name of the manufacturer on one side and a trade name and/or code marking for the medicament on the other side. In addition, they are easy to swallow, both when whole and in the form of fragments, that is to say, they are considerably easier to swallow than round or oval tablets or their fragments. Furthermore, it is also possible to manufacture divisible multi-layer retard tablets having different active substances and/or different types of active substance release, it being possible to arrange certain layers in such a manner that they have no points of fracture when the tablet is broken.

The divisible tablets according to the invention and the corresponding compacts can be described by the simplified general term "rod-shaped" because, as a result of their parallel side faces (ridges), they appear to be rods having an approximately rectangular to an approximately round cross-section. Rod-shaped in the narrower sense, that is to say biplanar, are compacts of the former type, in which the base and top faces, that is to say, the two faces defining the depth as being usually the smallest dimension of the tablet and those faces defining the width as being usually the mean dimension of the tablet are in each case flat, that is to say, corresponding faces are parallel to one another and are usually identical; tablets of this type and the corresponding compacts are called rod-shaped biplanar in the following. Compacts and tablets in which the two faces defining the depth as being the smallest dimension, or optionally the mean dimension, are convexly curved about the longitudinal axis or about parallels to this axis, and the two side faces are, as always flat, that is to say, parallel to one another, can be termed "capsule-shaped"; this type is called capsule-shaped biconvex in the following. Compacts in this latter form are especially suitable for the manufacture of corresponding film-coated dragees, that is to say, for the application of a film coating. The edges of the compacts or tablets, especially of those that are rod-shaped, are customarily bevelled or rounded. The face of the so-called ridge, which is formed by the mould wall in the pressing operation, preferably projects slightly from those faces of the tablet formed by the concave portion of the die. Mixed forms which are especially suitable for layer tablets are also those having, for example, a planar base face and a convex top face, the base face optionally having no dividing grooves or only shallow dividing grooves. The end faces can have any shape but with a view to ease of manufacture, on the one hand, and ease of swallowing the tablets on the other hand, they are preferably composed of a central portion that is curved about parallels to the axis of depth and corresponds to the ridge formed by the mould walls, and lower and upper portions that are also convex but at least partially almost spherically curved.

Advantageously, the ratio of the length to the depth of the tablet is from approximately 3:1 to 4.5:1 and the ratio of the width to the depth from approximately 1 to 1.6:1, especially from approximately 1.2 to 1.4:1, while the width constitutes preferably approximately ¼ to ½ of the length.

The divisible retard tablet according to the invention is provided on one or both sides with one or more dividing grooves running perpendicularly to the depth and the length, that is to say, in a transverse direction to the latter; dividing grooves that are provided on both sides are preferably opposite one another, but may, alternatively, be staggered, and also may be of the same or different depths. Accordingly the tablets can be divided into two or more predetermined equal or optionally unequal parts corresponding to, for example, a morning and an evening dose. This makes it possible to administer the medicament in individual doses that are adapted to the requirements, that is to say, to the syndrome and the patient, but that are nevertheless accurate. The depth of dividing grooves provided on one side or the total depth of dividing grooves provided on both sides is preferably approximately 2/5 to approximately ½ of the depth of the tablet, and the dividing grooves, which are formed by the dies, do not extend into the ridge formed by the mould wall, that is to say, into the planar side faces of the tablet. The side faces of the dividing grooves are preferably bevelled or curved. As a result of division, the surface area of such tablets is increased by a maximum of approximately 8% to approximately 12% if they can be divided into two fragments and by approximately 11% to approximately 16% if they can be divided into three fragments.

The divisible retard tablets according to the invention contain the customary adjuncts, optionally adapted to the active substance(s) used. Because of the increased breaking ability of the tablets and their tendency towards capping, it is preferable to use firmly coherent adjunct compositions on a matrix basis in order to be able to achieve a delayed and controlled release of the active substance.

The matrix material, which effects especially the delayed and controlled release of the active substance, can consist of an adjunct or adjunct mixture that is inert of indigestible per se, for example of plastics materials, such as polyvinyl chloride, acrylates and methacrylates. However, it can also be a material that is subject to progressive softening (for example, hydrophilic gel formers) or erosion in the course of the gastro-intestinal passage, (for example, lipids in admixture with inert carriers or digestible di- and triglycerides).

As retarding adjuncts it is possible to use substantially water-insoluble adjuncts or mixtures thereof, such as lipids, inter alia fatty alcohols, for example cetyl alcohol, stearyl alcohol and cetostearyl alcohol; glycerides, for example glycerin monostearate or mixtures of mono-, di- and triglycerides; vegetable oils; hydrogenated oils, such as hydrogenated castor oil or hydrogenated cotton seed oil; waxes, for example beeswax or carnauba wax; solid hydrocarbons, for example paraffin or mineral wax; fatty acids, for example stearic acid; certain cellulose derivatives, for example ethylcellulose or acetylcellulose; polymers or copolymers, such as polyalkylenes, for example polyethylene; polyvinyl compounds, for example polyvinyl chloride or polyvinyl acetate, and vinyl chloride/vinyl acetate copolymers and copolymers with crotonic acid, or polymers and copolymers of acrylates and methacrylates, for example copolymers of ethyl acrylate and methyl methacrylate. Adjuncts that are water-soluble or can be swelled with water and have the properties of retarding active substance release are, inter alia, suitable cellulose derivatives, especially corresponding ethers, for example methylcellulose, hydroxypropylcellulose, hydroxypropylmethylcellulose, or sodium carboxymethylcellulose (preferably those compounds having relatively high viscosity); certain polymers, such as polyacrylic acid and salts thereof; natural (anionic) mucous materials, for example xanthane, gum, guar gum, tragacanth or alginic acid and salts thereof, and the like.

The release of active substances that do not have especially good solubility in the neutral intestinal environment but have better solubility in the acid stomach region, may also be retarded by means of additives having functional carboxyl groups which dissolve in the neutral area, for example shellac, cellulose esters, for example cellulose acetate phthalate or hydroxypropylmethylcellulose phthalate, or semiesters of maleic acid anhydride copolymers.

In addition to the adjuncts that delay and control the release of the active substance, the divisible retard tablets of the present invention can also contain fillers and carriers that have no critical influence on the release of the active substance, such as, for example, bentonite (aluminium oxide/silicon oxide hydrate), talc, dicalcium and tricalcium phosphates, lactose, silicic acid, cellulose and similar adjuncts.

If desired, in addition to one or more active substances in an adjunct composition that effects a delayed and controlled release of the active substance, the divisible retard tablet according to the invention may contain one or more active substances that is or are released normally, that is to say, in a non-retarded manner; such an active substance or all such active substances generally is or are different from the first active substance to be released in a delayed manner but may, alternatively, be identical to the first active substance. Customarily, such an active substance is (or such active substances are) embedded in a customary adjunct, or preferably, in a mixture of customary adjuncts, such as fillers, disintegrating agents, binders and lubricants. Fillers, which customarily form the internal phase of a granulate, are, inter alia, sugars, such as lactose; starches, for example corn starch; phosphoric acid salts, for example, di- or tricalcium phosphate; cellulose (customarily microcrystalline cellulose) or derivatives thereof, and the like. Disintegrating agents, which form the outer phase of a granulate, are starches, for example corn starch, or derivatives thereof, for example sodium carboxymethyl starch, cellulose (for example, micro-crystalline cellulose) or derivatives, such as ethers thereof, for example sodium carboxymethylcellulose and the like. Binders are, inter alia, starch pastes, gelatins, cellulose derivatives, for example methylcellulose, and the like, while lubricants are, inter alia, stearic acid or suitable salts thereof, for example magnesium stearate or calcium stearate, talc, colloidal silicon oxide, and the like.

Divisible retard tablets according to the invention having several, for example two, tablet compositions for different types of active substance release, contain these compositions in different layers which, in order to ensure a uniform content of active substance in the fragments, run in the longitudinal direction of the tablet, that is to say, parallel to the plane defined by the directions of the length and the width.

As already mentioned, the divisible retard tablets according to the invention exhibit a surprisingly high strength, which makes it possible to apply a coating thus lending the finished tablet an additionally increased strength without impairing its ability to be divided. In addition, a coating may be necessary if the active substance or substances have an unpleasant taste, especially a bitter taste; the coating serves to mask the taste and thus makes the tablet easier to take.

The coating is customarily a soluble film coating that has no influence on the release of the active substance. The thickness of a soluble film coating is from approximately 20 $\mu$m to approximately 100 $\mu$m.

Especially suitable as film coating materials are suitable cellulose derivatives, such as cellulose ethers, for example methylcellulose, hydroxypropylcellulose or especially hydroxypropylmethylcellulose; mixtures of polyvinyl pyrrolidone or of a copolymer of polyvinyl pyrrolidone and polyvinyl acetate with hydroxypropylmethylcellulose; mixtures of shellac with hydroxypropylmethylcellulose, polyvinyl acetate or copolymers thereof with polyvinyl pyrrolidone; or mixtures of water-soluble cellulose derivatives, such as hydroxypropylmethylcellulose, and water-insoluble ethylcellulose. These actual coating agents may, if desired, be used in admixture with other adjuncts, such as talc, wetting agents, for example polysorbates (for example for facilitating application), or pigments (for example, for marking purposes). Depending on the solubility of the constituents, these coatings can be applied in aqueous solution or in organic solution (for example, solutions of shellac or ethylcellulose in organic solvents). Furthermore, it is also possible to use mixtures of acrylates that are water-insoluble per se, for example, the copolymer of ethyl acrylate and methyl methacrylate, which are used in aqueous dispersion, with water-soluble adjuncts, for example lactose, polyvinyl pyrrolidine, polyethylene glycol or hydroxypropylmethylcellulose.

The manufacture of the tablet composition consisting of active substances and adjunct composition, both of that having the delaying and controlling effect on the release of the active substance and of that for a normal release of the active substance takes place in customary manner, for example by forming a granulate and, if necessary, by adding suitable adjuncts, and using the customary mixing, pressing and coating apparatus. In the case of two-layer tablets in which the layers have, for example, different types of active substance release, it is customary first of all to prepress the lower half of the tablet having, for example, the properties of retarding the active substance release, and to press onto this the second, upper half of the tablet having, for example, a normal type of active substance release, and then to press the two layer tablet together to form the finished article.

Especially preferred is a divisible retard tablet consisting of a compact which is optionally provided with a coating and contains an active substance in an adjunct composition that effects a delayed and controlled release of the active substance, or contains, in two different layers, an active substance in an adjunct composition that effects a delayed and controlled release of the active substance and a second active substance in an adjunct composition that does not significantly influence the release of the active substance, the shape of the compact being characterised in that the ratio of length to width to depth is approximately 3 to 4.5:approximately 1 to 1.6:1, and the width constitutes approximately $\frac{1}{4}$ to $\frac{1}{2}$ of the length, either one or two dividing grooves are present which lie opposite one another, run perpendicularly to the length and the depth and have a total depth constituting approximately 2/5 to approximately $\frac{1}{2}$ of the depth of the tablet, and the other shape characteristics correspond to those given above, but a tablet that is capsule-shaped in the sense given above being especially preferred. On dividing tablets having the afore-mentioned dimension ratios, the total surface area of the fragments in comparison with the total surface area of the undivided tablet is increased by from approximately 8% to approximately 12%. The adjunct composition effecting a delayed and controlled release of the active substance preferably contains a polymeric or copolymeric adjunct having retarding properties, especially polymers or copolymers of acrylates or methacrylates, such as a copolymer of ethyl acrylate and methyl methacrylate.

The composition of the new divisible retard tablets of the present invention and the manufacture thereof is illustrated and described in more detail inter alia, in the following Examples.

The Figures illustrate examples of the different forms of the divisible retard tablets according to the invention.

FIG. 1 shows a rod-shaped biplanar tablet that is provided on both sides with dividing grooves [1a: longitudinal view; 1b: end view and 1c: top view; x: length; y: width; (a: ridge) and z: depth (usually the smallest dimension)], and can be divided into two equal fragments.

FIG. 2 shows a capsule-shaped biconvex divisible retard tablet that is provided on both sides with dividing grooves, is provided with a coating (b) and can be divided into two equal fragments; (2a: longitudinal section; 2b: end view and 2c: top view).

Figure 3A:
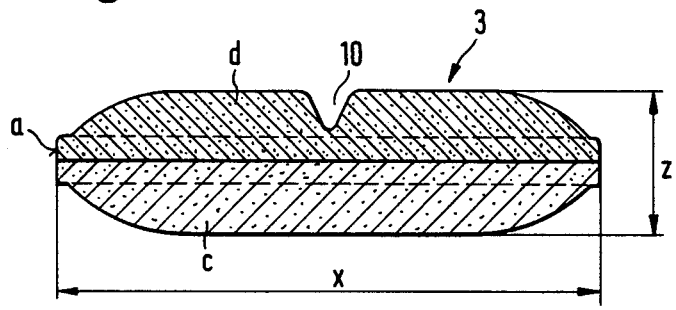
Figure 3B:
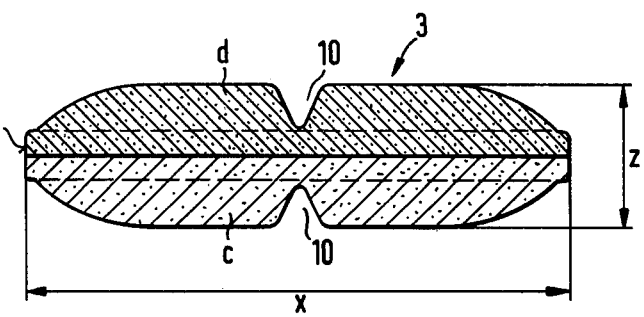
Figure 3C:
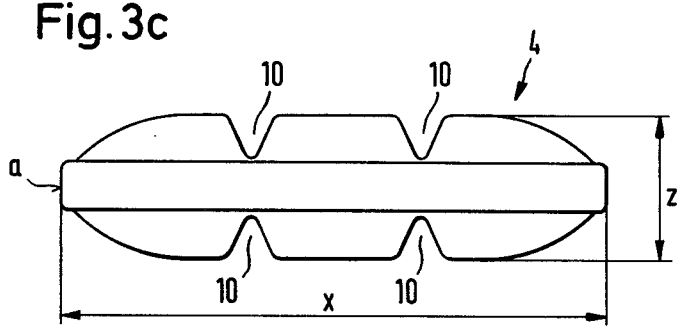
Figure 3D:
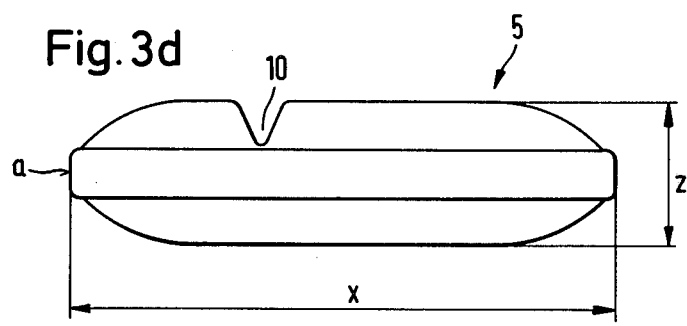
Figure 3E:
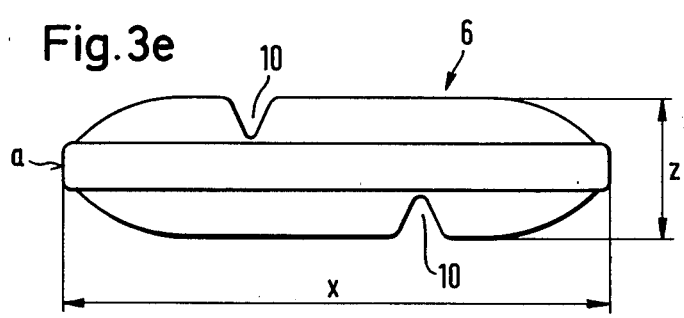

FIG. 3 shows side views of different forms of the tablets according to the invention: two-layer and capsule-shaped biconvex divisible retard tablets having a notch provided on one side (3a) or notches provided on two sides (3b), in which, for example, layer c has properties of delaying and controlling the release of the active substance, while the active substance or substances is or are released from layer d without delay or control; capsule-shaped biconvex retard tablet (3c) that can be divided into three fragments and is provided with dividing notches on both sides; capsule-shaped biconvex retard tablet (3d) that can be divided into two fragments of unequal size and is provided on one side with a dividing notch; and capsule-shaped biconvex retard tablet (3e) that can be divided into three fragments and is provided on both sides with staggered dividing notches.

EXAMPLE 1

A mixture of 2.0 kg of the tartrate of 1-[4-(2-methoxyethyl)phenoxy]-3-isopropylaminopropan-2-ol (metoprolol), 0.1 kg of colloidal silicon dioxide, 0.2 kg of calcium biphosphate and 0.25 kg of micro-crystalline cellulose is granulated with 0.6 kg of a 30% aqueous dispersion of the 70:30 copolymer of ethyl acrylate and methyl methacrylate in the fluidised bed. The spraying-in speed is 300 ml per minute at a supply air temperature of 30° C. Drying is carried out subsequently in the same apparatus for 20 minutes at a supply air temperature of 40° C. The granulate is placed in a planetary mixer and 0.8 kg of stearyl alcohol, melted and heated to 60° C., is added and the whole is kneaded for 15 minutes. After cooling, the granulate is pressed through a sieve of 1 mm mesh width and mixed for 10 minutes in a tumbler mixer with 0.05 kg of magnesium stearate, 0.05 kg of colloidal silicon dioxide and 0.4 kg of hydroxypropyl-methylcellulose (viscosity 15 000 cps).

The pressing of the retard granulate thus obtained to form capsule-shaped biconvex tablets each having a gross weight of 445 mg is carried out on a tablet press having guided dies of the following dimensions: length 17.0 mm, width 8.0 mm and radius of curvature 4.8 mm, one of the two opposing dies including a wedge which has a height of 2.0 mm (in relation to the depth of the concave portion) and forms a tapering dividing notch (wedge angle: 45°–60°), or each of the two opposing dies having a wedge of 1.1 mm height (in relation to the depth of the concave portion) which forms the desired dividing notch. The total depth of the resulting compacts is approximately 4.6 mm.

Coating is carried out in a coating vessel of 55 cm diameter which is equipped with baffle plates. With the aid of a binary nozzle 5 kg of compacts are sprayed continuously with a coating solution or suspension of the following composition. 0.1 kg of hydroxypropylmethylcellulose (viscosity 5 cps) are dissolved in 1.2 kg of demineralised water. To this there are added while stirring, 0.005 kg of polysorbate 80, 0.05 kg of talc and 0.1 kg of a 20% homogeneous suspension of titanium dioxide in a solution of 0.007 kg of hydroxypropylmethylcellulose (5 cps) in 90% ethanol. The supply air temperature is 60° C.; the temperature of the compacts in the vessel is maintained at approximately 35° C. The amount of film coating sprayed on is 19 mg (dry weight) per compact.

The dissolving speed of the film-coated tablets is determined by the diameter method (Langenbucher and Rettig, Drug. Dev. Ind. Pharm., 3, 241 [1977]), at a flow rate of 16 ml per minute using artificial gastric juice (pH 1.2, without enzymes) for the first hour, and then using artificial intestinal juice (pH 7.5, without enzymes) at 37° C. The following results were obtained for the release of the active substance from the whole and halved film-coated tablets as a percentage of the theoretical content:

| time: | whole tablet: | halved tablet: |
| --- | --- | --- |
| 60 min | 23% | 27% |
| 120 min | 38% | 43% |
| 240 min | 57% | 65% |
| 360 min | 72% | 78% |

EXAMPLE 2

The retard granulate of the tartrate of 1-[4-(2-methoxyethyl)phenoxy]-3-isopropylaminopropan-2-ol (metoprolol) is manufactured as described in Example 1.

At the same time, the following non-retarding granulate is manufactured:

A mixture of 0.25 kg of 3-(4-chloro-3-sulphamoylphenyl)-3-hydroxy-isoindolin-1-one (chlortalidone), 1.75 kg of lactose and 0.5 kg of corn starch is worked into a plastic mass together with 0.3 kg of a paste consisting of 0.1 kg of corn starch and 0.2 kg of water in a planetary mixer. The moist mass is forced through a sieve of 2 mm mesh width and dried in the fluidised bed for 20 minutes at 60° C. The dried granulate, forced through a sieve of 1 mm mesh width, is mixed with 0.1 kg of talc, 0.01 kg of magnesium stearate and 0.29 kg of micro-crystalline cellulose.

The pressing of the two granulates to form a capsule-shaped biconvex tablet is carried out on a tablet machine having guided dies which makes it possible to manufacture layer tablets. First, the non-retarding granulate is metered in and then the retard granulate from a second filling funnel. For pressing, two dies for two different dividing notches are used having the following dimensions: length 19.0 mm, width 7.0 mm and radius of curvature 4.2 mm. The tapering dividing notches in the compact are 1.7 mm in depth (concave depth) on the side of the retard layer and 0.8 mm in depth on the side of the chlortalidone layer. A tablet depth of approximately 6 mm is produced.

The release of metoprolol tartrate from the retard layer takes place in the manner given in Example 1; the disintegration time of the non-retarding chlortalidone layer is 2–3 minutes (disintegration testing apparatus according to U.S. Pharmacopoeia, artificial gastric juice at 37°).

EXAMPLE 3

A mixture of 9.6 kg of the ground hydrochloride of 1-(2-allyloxyphenoxy)-3-isopropylaminopropan-2-ol (oxprenolol) and 6.98 kg of ground lactose is granulated together with 16.0 kg of a 30% aqueous dispersion of the 70:30 copolymer of ethyl acrylate and methyl methacrylate in the fluidised bed; the spraying-in speed is 0.7 liter/minute and the temperature of the supply air is 38°. The mixture is then dried in the same apparatus for 25 minutes at a supply air temperature of 40° C. With the simultaneous addition of 0.12 kg of colloidal silicon dioxide, 0.3 kg of calcium stearate and 4.0 kg of stearic acid, the granulate is forced through a sieve of 1 mm mesh width and then mixed in a planetary mixer for 15 minutes.

The pressing of the granulate to form capsule-shaped biconvex tablets each weighing 410 mg is carried out on a tablet press having guided dies (the two opposing dies being provided with wedges for forming the dividing notches) having the following dimensions: length 16.5 mm, width 6.0 mm, and radius of curvature 3.6 mm. The tapering dividing notches provided on both sides are each 1.47 mm in depth; the depth of the compact is approximately 5.4 mm.

The compacts so obtained are coated with a film as described in Example 1.

The dissolving speed is measured according to the method described in Example 1 and the results are as follows:

| time: | whole tablet: | halved tablet: |
|---|---|---|
| 60 min | 32% | 36% |
| 180 min | 62% | 68% |
| 300 min | 80% | 86% |
| 420 min | 92% | 96% |

EXAMPLE 4

The retard granulate of the hydrochloride of 3-(2-allyloxyphenoxy)-3-isopropylaminopropan-2-ol (oxprenolol) is manufactured as described in Example 3.

At the same time, a conventional granulate is prepared as follows:

15.6 kg of 3-(4-chloro-3-sulphamoylphenyl)-3-hydroxy-isoindolin-1-one (chlortalidone), 3.0 kg of microcrystalline cellulose, 6.456 kg of dicalcium phosphate, 0.9 kg of corn starch, 0.024 kg of iron yellow and 0.120 kg of magnesium stearate are homogeneously mixed.

The pressing of the two active substance mixtures to form capsule-shaped tablets is carried out as described in Example 2. The tablets have a lenth of 18.0 mm, a width of 5.5 mm, a depth of approximately 5.6 mm and a radius of curvature of 3.5 mm; the depth of the dividing notches provided on both sides is 1.47 mm in each case.

The release of the hydrochloride of oxprenolol takes place in the manner described in Example 3, whilst the disintegration time of the non-retarding chlortalidone layer is approximately 1 to 2 minutes (disintegration testing apparatus according to U.S. Pharmacopoeia in artificial gastric juice at 37°).

We claim:

1. A divisible tablet having controlled and delayed release of the active substance, characterised in that it consists of a compact, with or without a coating having no influence on the release of said active substance, said compact being formed by pressing a granulate of at least one active substance and an adjunct composition which effects the controlled and delayed release of the active substance to form a granulate-retard matrix, with or without one or more additional granulate adjunct compositions which contain an active substance or do not contain such active substance and are arranged in longitudinal layers, the compact being of an oblong shape in which the ratio of length to width to depth is approximately 2.5 to 5:approximately 0.9 to 2:1 and the width constitutes at most ⅔ of the length, and in which one or more deep dividing groves are present which run perpendicularly to the length and depth and have a total depth of from approximately ⅓ to approximately ½ of the depth of the tablet, but are at least so deep that one fracture surface area multiplied by the number of possible fragments constitutes a maximum of 15% of the surface area of the undivided tablet, the base and top faces independently of one another are planar or are convexly curved about the longitudinal axis or about parallels to this axis, the side faces are planar, the end faces can be of any shape and with or without bevelled or rounded edges.

2. Tablet according to claim 1, characterised in that it consists of a compact with or without a coating and is formed by an active substance in an adjunct composition that effects a delayed and controlled release of the active substance and with or without an additional adjunct composition that contains an active substance, is arranged in a longitudinal layer and does not significantly influence the release of the active substance, the compact being of an oblong shape in which the ratio of length to width to depth is approximately 3 to 4.5:approximately 1 to 1.6:1 and the width constitutes approximately ¼ to ½ of the length, either one or two dividing grooves are present which lie opposite one another, run perpendicularly to the length and depth and have a total depth constituting approximately 2/5 to approximately ½ of the depth of the tablet, and in which the other shape characteristics correspond to those of claim 1.

3. Tablet according to claim 2, characterised in that it consists of a compact having the shape characteristics of claim 2, with or without a coating and is formed by an active substance in an adjunct composition that effects a delayed and controlled release of the active substance.

4. Tablet according to claim 2, characterised in that it consists of a compact having the shape characteristics of claim 2, with or without a coating and is formed by an active substance in an adjunct composition that effects a delayed and controlled release of the active substance and an additional adjunct composition that contains an active substance, is arranged in a longitudinal layer and does not significantly influence the release of the active substance.

5. Tablet according to one of claims 2, 3 and 4, characterised in that the base and top faces of the tablet are planar and parallel to one another.

6. Tablet according to one of claims 2, 3 and 4, characterised in that the base and top faces of the tablet are convexly curved about the longitudinal axis or about parallels to this axis.

7. Tablet according to one of claims 1, 2, 3, 4, 5, or 6, characterised in that the adjunct composition effecting a delayed and controlled release of the active substance contains a polymeric or copolymeric adjunct having retarding properties.

* * * * *